United States Patent [19]
Andersson-Engels et al.

[11] Patent Number: 5,115,137
[45] Date of Patent: May 19, 1992

[54] DIAGNOSIS BY MEANS OF FLUORESCENT LIGHT EMISSION FROM TISSUE

[75] Inventors: Stefan Andersson-Engels, Hoor; Jonas Johansson, Lund; Unne Stenram, Lund; Katarina Svanberg, Lund; Sune Svanberg, Lund, all of Sweden

[73] Assignee: Spectraphos AB, Lund, Sweden

[21] Appl. No.: 598,716

[22] PCT Filed: Feb. 21, 1990

[86] PCT No.: PCT/SE90/00118
§ 371 Date: Nov. 28, 1990
§ 102(e) Date: Nov. 28, 1990

[87] PCT Pub. No.: WO90/10219
PCT Pub. Date: Sep. 7, 1990

[30] Foreign Application Priority Data
Feb. 22, 1989 [SE] Sweden .................. 8900612

[51] Int. Cl.⁵ .......................... G01N 21/64
[52] U.S. Cl. .................. 250/461.2; 128/633; 128/634
[58] Field of Search .............. 128/634, 633; 250/461.2

[56] References Cited
U.S. PATENT DOCUMENTS 4,682,594 7/1987 Mok ........................ 606/7
4,718,417 1/1988 Kittrell et al. ............... 606/7
4,768,513 9/1988 Suzuki ..................... 128/634
4,785,806 11/1988 Deckelbaum ............... 606/7
4,786,813 11/1988 Svanberg et al. .......... 250/461.1

FOREIGN PATENT DOCUMENTS
WO86/02730 5/1986 PCT Int'l Appl.
2125986 3/1984 United Kingdom.

OTHER PUBLICATIONS
Anon., "A New Instrument for Rapid Measurement of Blood Oxygen Saturation and Hb Concentration", Bio-Medical Engineering (GB), vol. 5, No. 11 (Nov. 1970) pp. 549–552.

Primary Examiner—Constantine Hannaher
Attorney, Agent, or Firm—Young & Thompson

[57] ABSTRACT

A sample (1) is irradiated by a pulse from a laser (2), creating fluorescence radiation, which is brought, in imaging relation or otherwise, to a detector (6) sensing from the same sample (1) in a plurality of spectral intervals (6A-6D), for obtaining intensity values. The radiation may be sensed in imaging relation, creating a multiplicity of said pluralities. The spectral intervals may be wavelength defined by passband filters (5A-5D) or time interval defined time spectral intervals controlled by a computer (7), which makes a numerical evaluation comprising a division. The tissue character may then be evaluated from the evaluation.

10 Claims, 15 Drawing Sheets

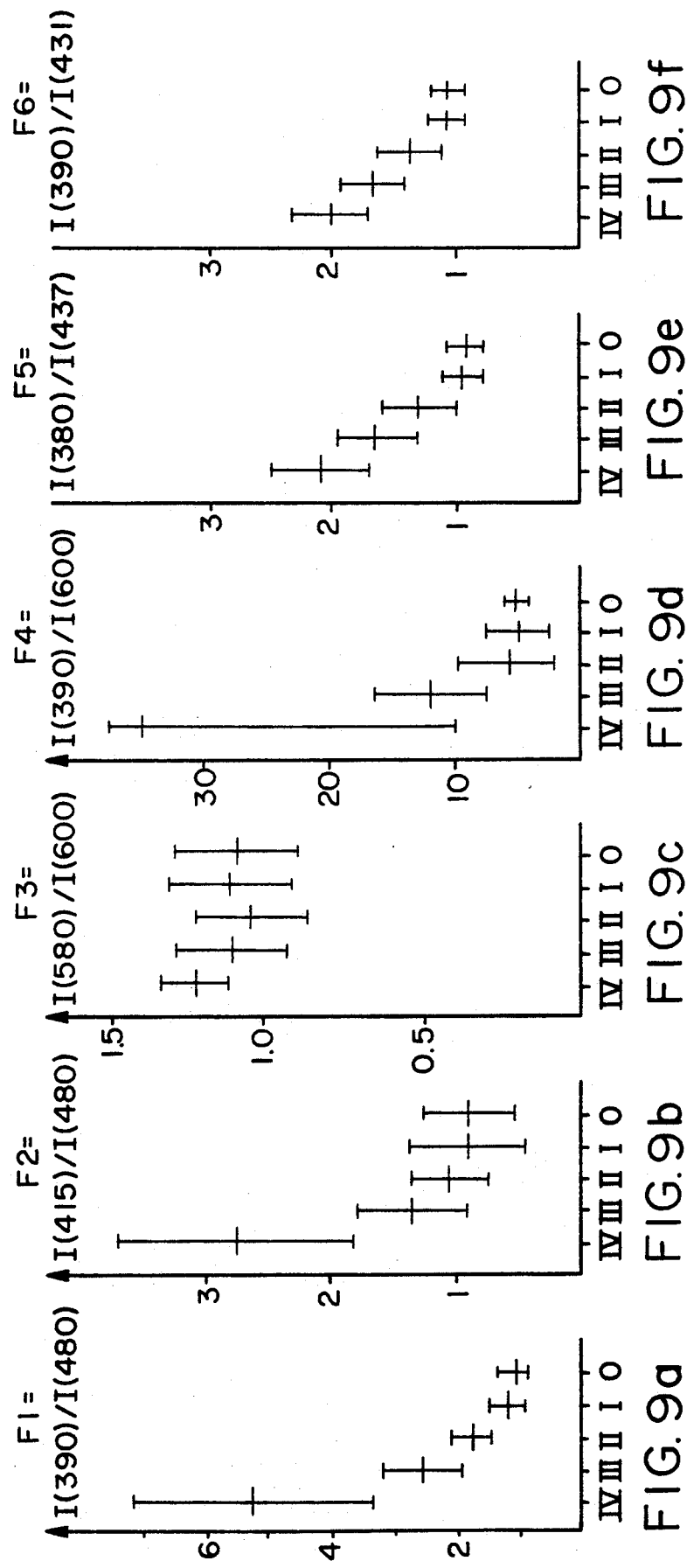

DIAGNOSIS BY MEANS OF FLUORESCENT LIGHT EMISSION FROM TISSUE

FIELD OF THE INVENTION

The present invention regards improved detection of properties of tissue by means of induced fluorescence.

DESCRIPTION OF THE RELATED ART

It is known from e.g. U.S. Pat. Nos. 4,682,594 and 4,785,806, hereby included by reference, to introduce an optical fiber into a blood vessel, e.g. an artery, irradiate with laser light and sense the induced fluorescent light. It is then possible to detect atherosclerotic plaque, which can then be destroyed and removed by irradiating with high-power laser energy through the same optical fiber. The mentioned patents disclose the means for exciting, spectral analysis and high-power irradiation, including beam-splitters, coupling means and laser devices.

In EP-A-0 199 767 (which corresponds to U.S. Pat. No. 4,786,813), there is described an imaging fluorescence detecting device where a sample irradiated with an excitation wavelength is imaged through a beam-split device into a plurality of images, the images being filtered before hitting a matrix detector (CCD detector). For each image, a set of corresponding pixel intensity values is obtained, which can be arithmetically treated to obtain combined pixel values. The combined pixel values are used to create an image with improved contrast.

For fluorescence study of tissue, the fluorescent behavior of different tissues is used. In some cases, contrast may be enhanced by administering substances like hematoporphyrin derivates. A disadvantage therewith is that the patient may be hypersensitized to sunlight for extended periods, and it is thus an object of the invention to increase the detection contrast in order to diminish the necessary administering dose.

SUMMARY OF THE INVENTION

It is a general object of the invention to enable maximum contrast in fluorescence detection.

It is also an object of the present invention to improve the recognition possibilities in in vivo diagnosis of various states and variations of tissue, for example for detecting atherosclerotic plaque and various malignant tumours. It is a further object to improve treatment possibilities when removing or destroying tissue by irradiation, by means of improved possibility of study before, during and after treatment. A further object is to enable avoidance of destruction of tissue which should be left unharmed.

It is a particular object of the invention to enable detection even in the presence of blood. Blood present as an absorbent will act as a differential absorber of fluorescent radiation, destroying the contrast obtainable, severely distorting the diagnostic information. With the present invention, it is possible to substantially eliminate the influence of this disturbance factor.

According to an important aspect of the invention, the objects of the invention are attained by a combination of laser light source means for fluorescence excitation, a light detector, a light conductor like an optical fiber, coupling means for entering laser light into one end of the light conductor and for taking out light therefrom into the detector, and diagnostic means coupled to the detector, which enable the study of fluorescent light in a plurality of spectral interval channels and the comparison of the channels. This combination may be suitably completed by means for irradiation with high power through the same optical fiber, such that e.g. destruction and removal can be combined with successive recognition steps, such that the removal can be under control. The same laser may be used for both diagnostics and irradiation with high power, if the laser energy is adjusted accordingly.

According to another aspect of the invention, the system may be enlarged into an imaging system, whereby a multiple pixel system enables two-dimensional imaging, whereby for each pixel a signal is obtained for a plurality of spectral fluorescence intervals.

In this disclosure, spectral fluorescence intervals are meant to comprise both intervals in wavelength and intervals in time. In the latter case, the radiation which induces fluorescence has the form of short pulses, or at least an irradiation which can be stopped in a very short time interval. Detection can then be made of the distribution in time of the diminishing fluorescence radiation, which diminishing is caused by the different lifetimes of excited states, which in turn are characteristic of different substances which are proper for tissues of different kinds.

A particular feature of the invention resides in the use of arithmetic operations on intensity values, which comprise division. By division of two values having the dimension of intensity, it is possible to obtain normalized or dimensionless values, compensating largely for variations in intensity, distance, angle and other variables which may otherwise falsify the results.

When intervals in time are used, it is preferred to utilize a pulsed laser, or at least a laser having a rapid cutoff. Although a continuous laser may be used when detecting without using time interval windows, it may still be interesting to use a pulsed laser in that case in order to simplify elimination of spurious radiation due to imperfections in spectral resolution.

BRIEF DESCRIPTION OF THE DRAWINGS

The invention will now be described by reference to Examples and embodiments shown in the drawings.

FIGS. 9a-9f depict the efficiency of various wavelength selections in differentiating between normal vessel (O) and four increasingly more damaged atherosclerotic classes of vessels (I–IV).

DESCRIPTION OF THE PREFERRED EMBODIMENTS

Figure 1A:
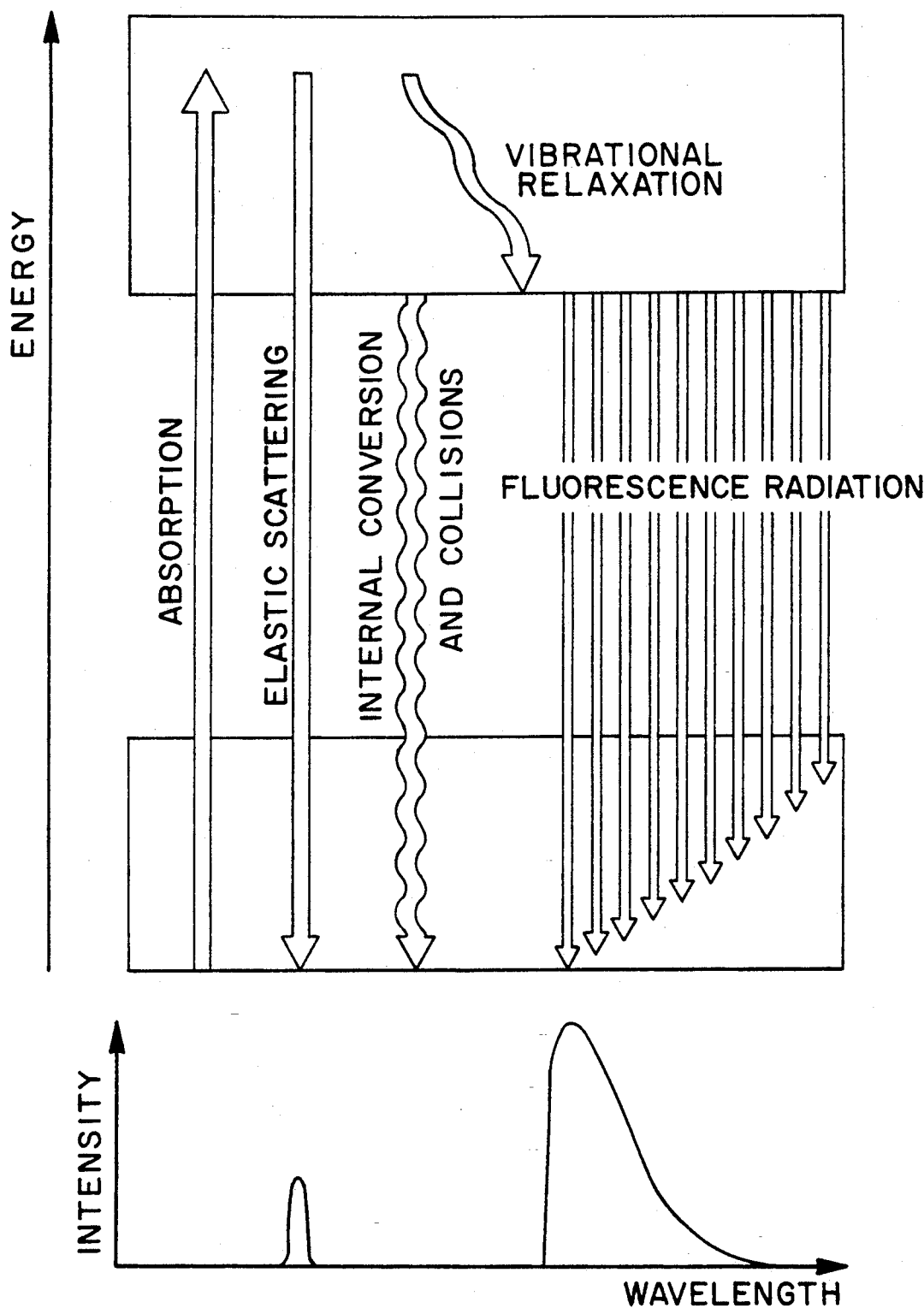
FIGS. 1a and 1b illustrate the mechanism of fluorescence radiation.

FIG. 1a schematically illustrates the mechanism of fluorescence in large molecules. An irradiated sample will absorb radiation, and various levels will be excited. Some of the states will return back substantially to the previous state (elastic scattering), some will be lost in internal conversion, collisions and other loss mechanisms. Some, however, will create fluorescent radiation, which, due to the distribution of states will give a broad wavelength distribution as seen in the schematic intensity spectrum below in FIG. 1a.

Figure 1B:
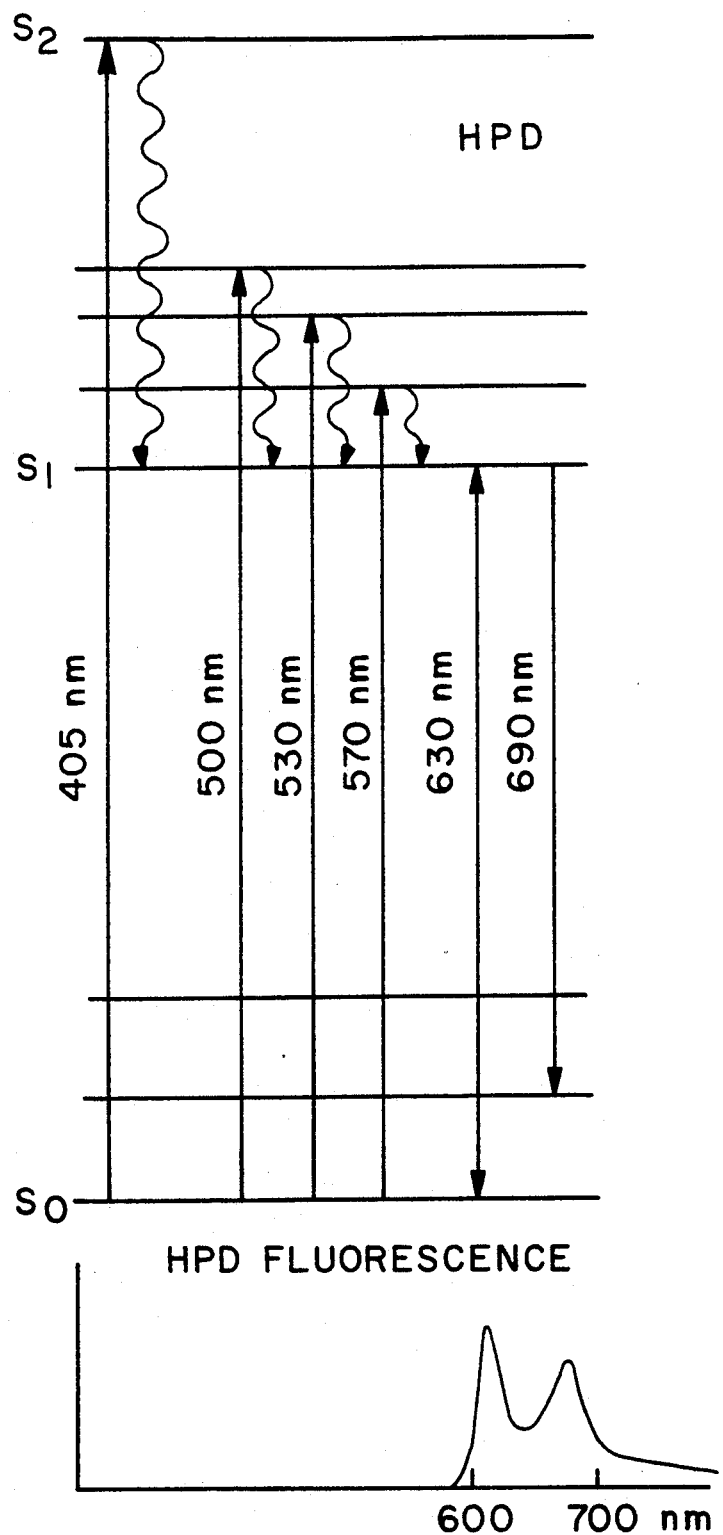
Figure 2:
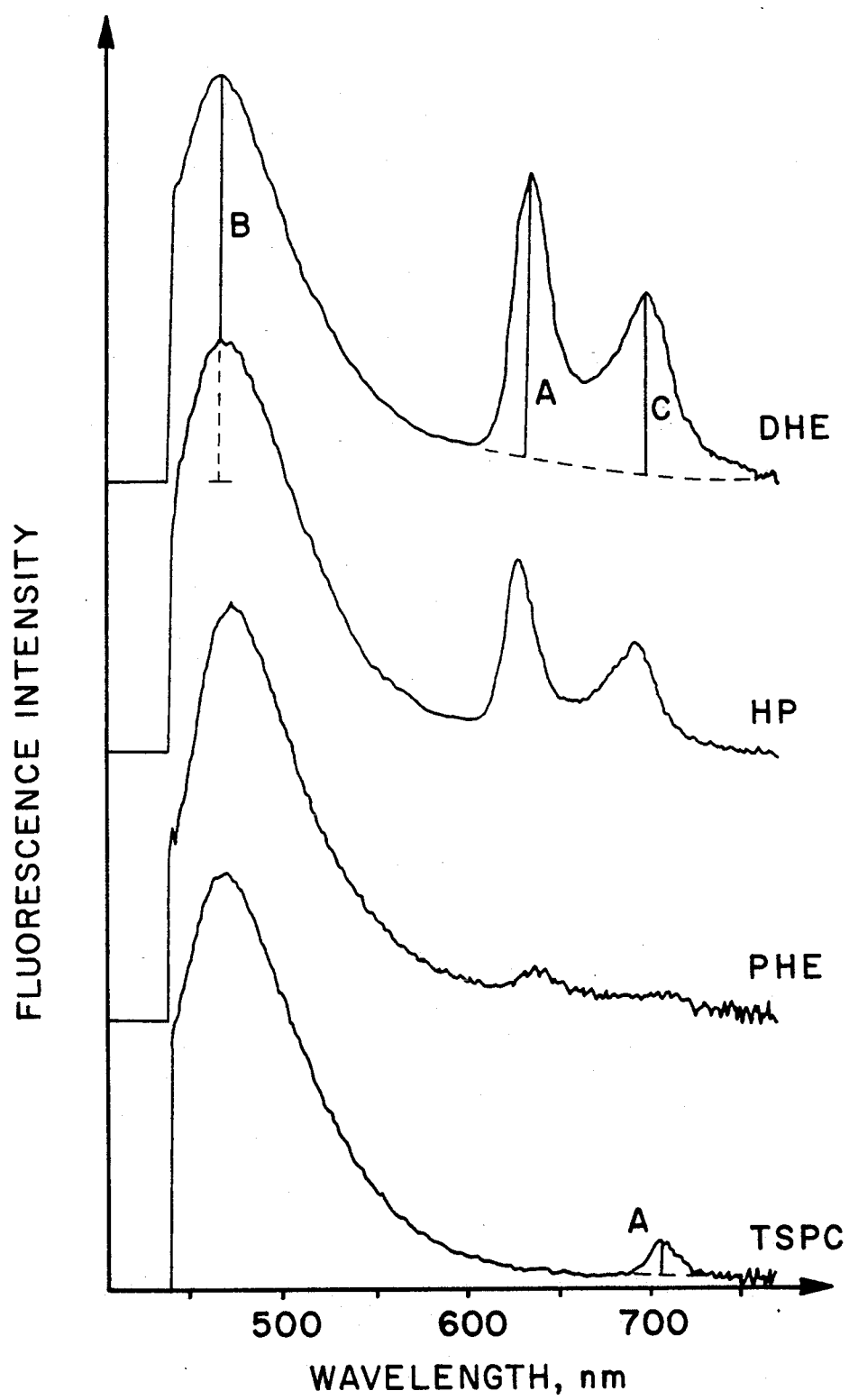
FIG. 2 shows wavelength spectra for a number of tumour marking agents.

Some useful tumour-marking agents such as hematoporphyrin derivatives (HPD) give more structured fluorescence spectra as of FIG. 1b, particularly if excited in the Soret band around 405 nm. The fluorescence spectrum shows typical peaks at about 630 and 690 nm, superimposed in practice on more unstructured tissue autofluorescence. There are other known examples of such agents. FIG. 2 shows fluorescence spectrograms for substances irradiated at 337 nm ($N_2$ laser) for DHE (dihematoporphyrin ether/ester), HP (hematoporphyrin), PHE (polyhematoporphyrin ester), and TSPC (tetrasulfonated phthalocyanine).

Figure 3A:
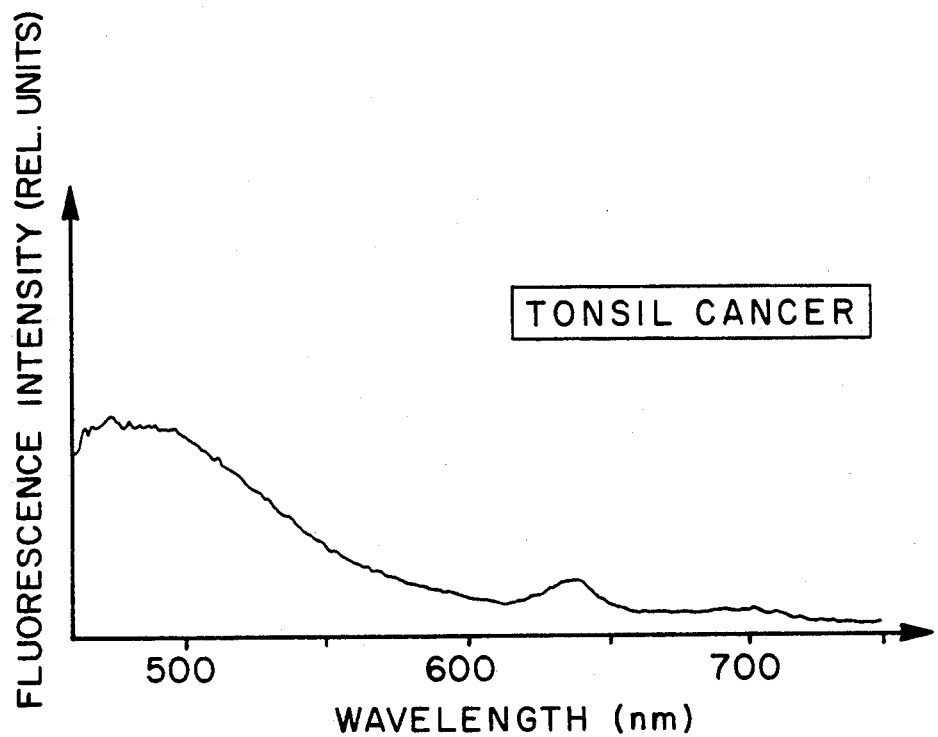
FIG. 3a shows the wavelength fluorescence spectra of a cancerous tissue.
Figure 3B:
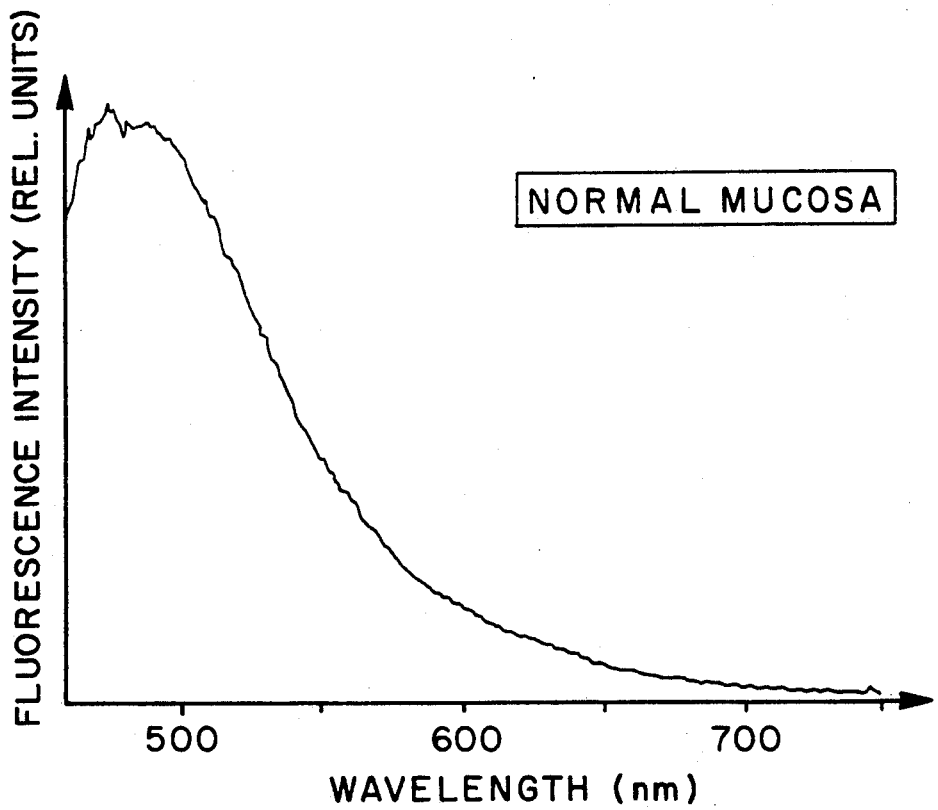
FIG. 3b shows the wavelength fluorescence spectra of a healthy tissue.

Another example of difference in wavelength spectra of different tissues is shown in FIG. 3, where the spectrum for tonsil cancer is clearly different from normal mucosa, due to endogenous porphyrins.

EXAMPLE I

A mode-locked argon-ion laser (Coherent Radiation CR-12) was used to synchronously pump a Coherent Radiation dye laser equipped with a cavity dumper. The dye laser provided 6 ps long pulses at 640 nm at a repetition rate of about 3 MHz. The average power was about 10 mW. The red pulses were frequency doubled to 320 nm in a KD*P crystal with an efficiency of the frequency doubling of approximately 0.5%. Fluorescence light was wavelength selected in a 0.5 m spectrometer together with interference filters, and was detected in a microchannel plate photomultiplier tube (Hamamatsu 1564 U). The electronics included a starting pulse channel, and suitable signal amplifiers, constant fraction discriminators and a time-to-amplitude converter were employer. Time histograms were built up in a multichannel analyser and data analysis was performed with a program package on an IBM-compatible personal computer. The time response function of the apparatus was measured with scattered light and found to have a FWHM=250 ps. This value was used in the computer deconvolution procedure of the fluorescence signal.

Figure 4:
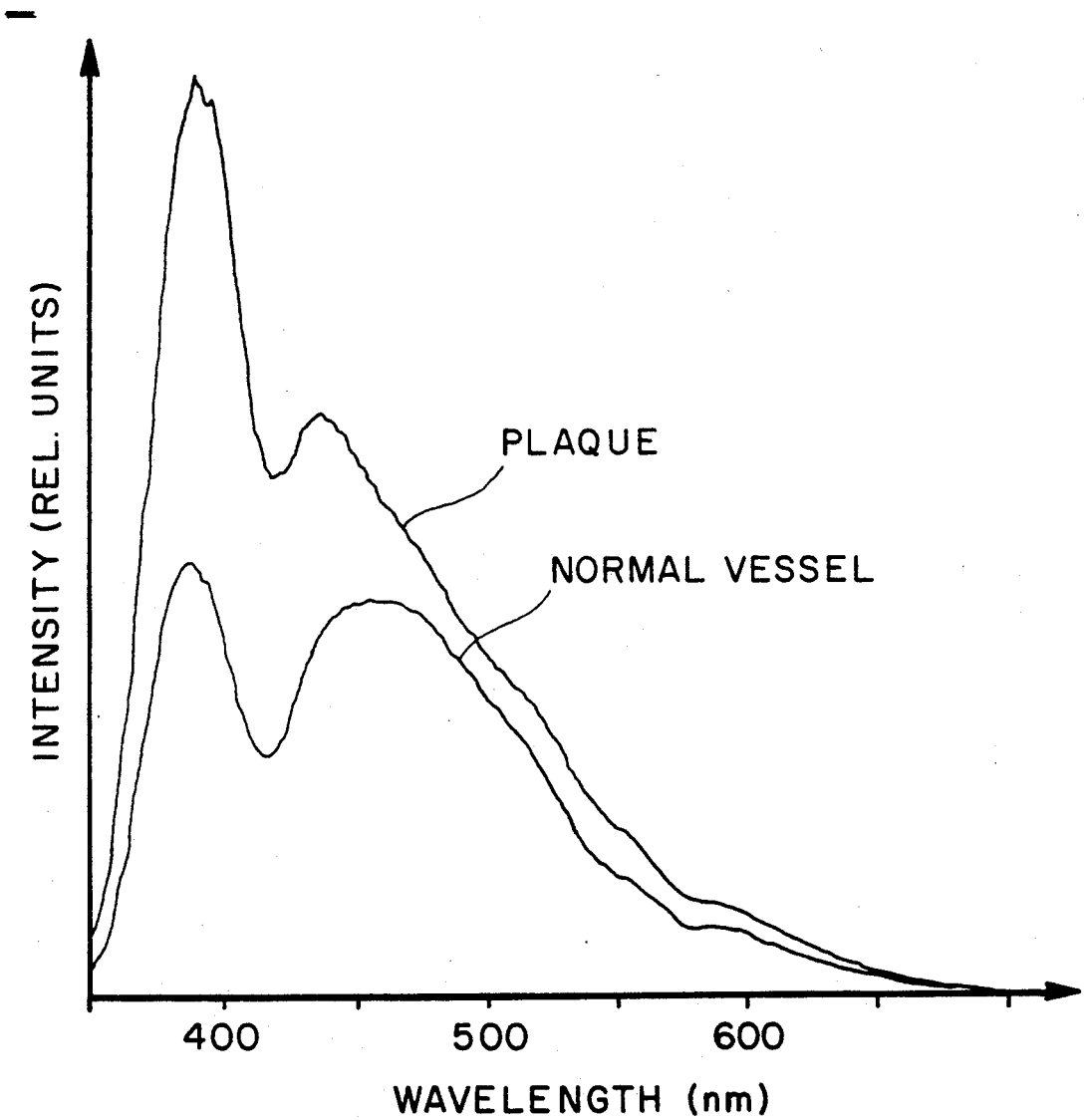
FIG. 4 shows the difference in wavelength fluorescence spectra between blood vessels with and without plaque.

Data were recorded in scans starting in a normal blood vessel wall and passing over an atherosclerotic plaque region. The sample was moved on a micrometer-controlled sledge to allow reproducible positioning of the sample in time-resolved recording scans at different fluorescence wavelength. Typically, decay curves were recorded during 2 min. at a count rate of about 1000 Hz. The typical time-integrated fluorescence structures of normal vessel wall and plaque are shown in FIG. 4.

Figure 5A:
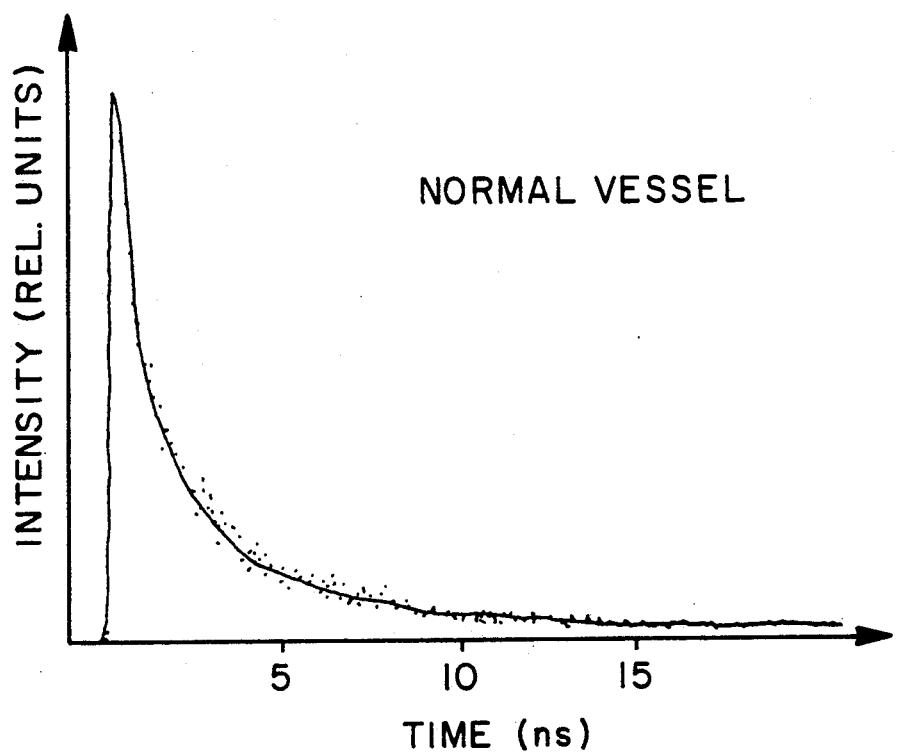
FIG. 5a shows the time spectra for a selected wavelength for a normal vessel.
Figure 5B:
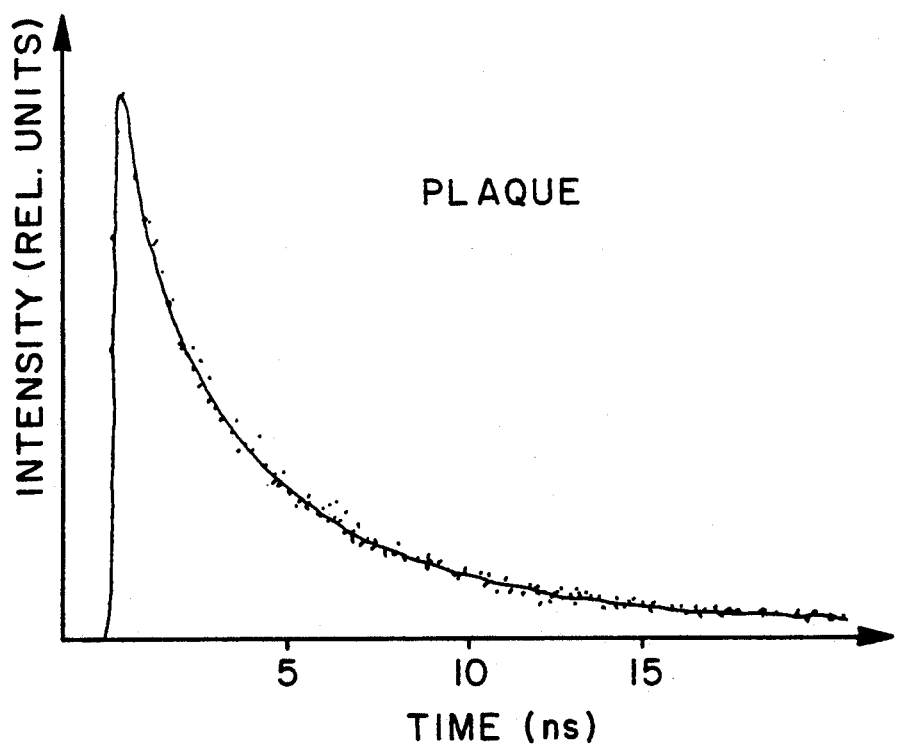
FIG. 5b shows the time spectra for a selected wavelength for a vessel with plaque.

Time-resolved recordings of sample fluorescence at 400 nm are shown for plaque and normal tissue wall in FIG. 5. Clear differences in the temporal behaviour can be observed. Three different lifetimes of approximately 8 ns. 2 ns and one shorter than 200 ps are observed for both plaque and normal vessel.

Figure 6A:
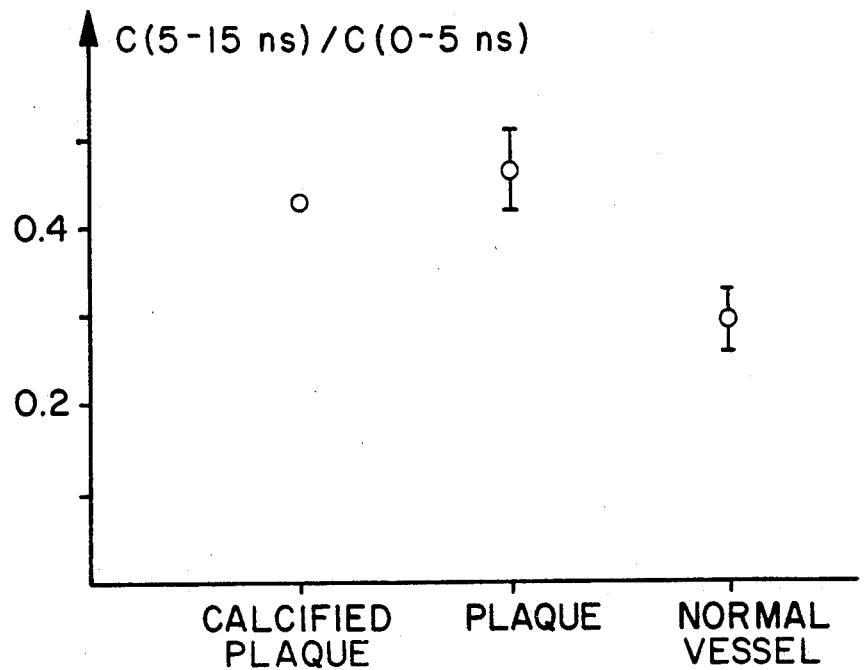
FIGS. 6a and 6b show results of divisions between time spectrum signals for equal wavelengths for plaque and healthy vessel.
Figure 6B:
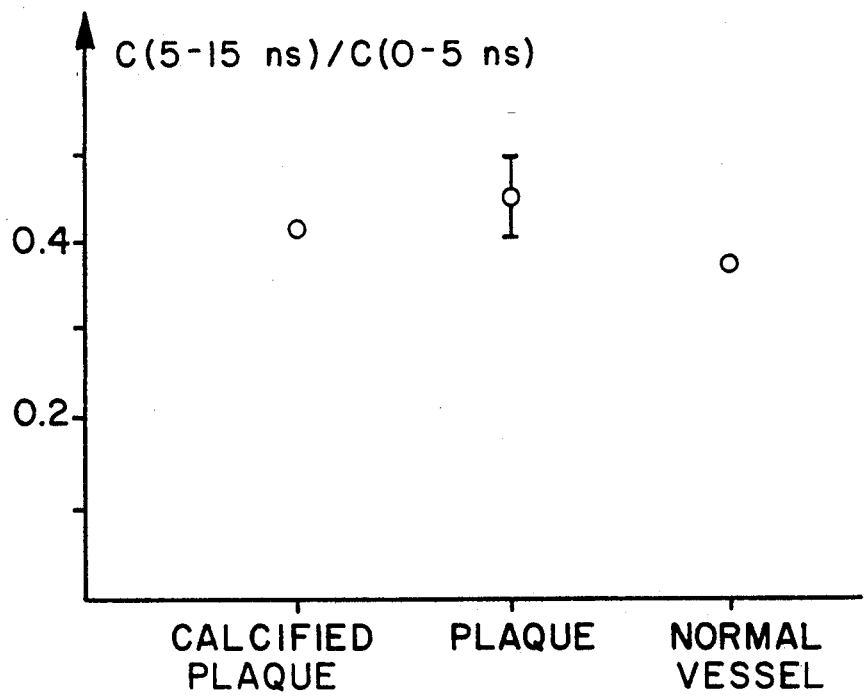
Figure 7:
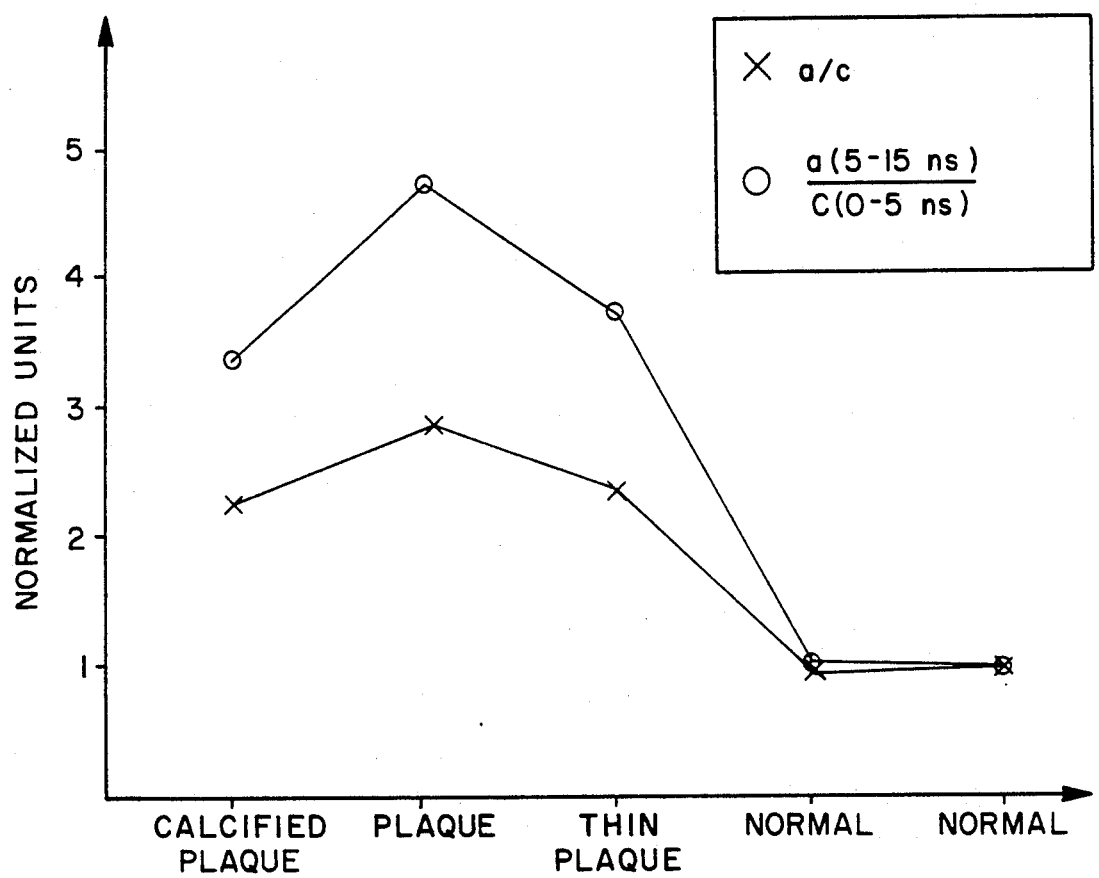
FIG. 7 shows results of divisions for two wavelengths with and without time spectrum analysis.

Data from plaque, calcified plaque and normal vessel wall are shown in FIG. 6. The monochromator was set to 400 nm and 480 nm, corresponding to two characteristic wavelengths. The fluorescence intensities at 400 nm and 480 nm are denoted a and c, respectively. Here, the signal integrated from 5 ns to 15 ns is divided by the signal obtained from the first 5 ns of the decay. For a fast decay, this ratio obviously has a low value, whereas higher ratios indicate a slower decay. A plaque demarcation ratio of 1.6:1 is obtained when measuring the a-signal, while the demarcation ratio is lower for the c-signal. This feature can be included in a suitable demarcation criterion. If this temporal behaviour is used in forming the dimensionless demarcation function a (5–15 ns)/c(0–5 ns) instead of the time-integrated quantities, a demarcation improvement of 1.6 is obtained. A scan through a plaque region is shown for the time-integrated, as well as the time-resolved demarcation criterion in FIG. 7, showing a demarcation improvement from 2.8 to 4.5.

This Example shows the value of a resolution in two dimensions (wavelength and time) of fluorescence detection in order to enhance the resolution of tissue differences.

Figure 8A:
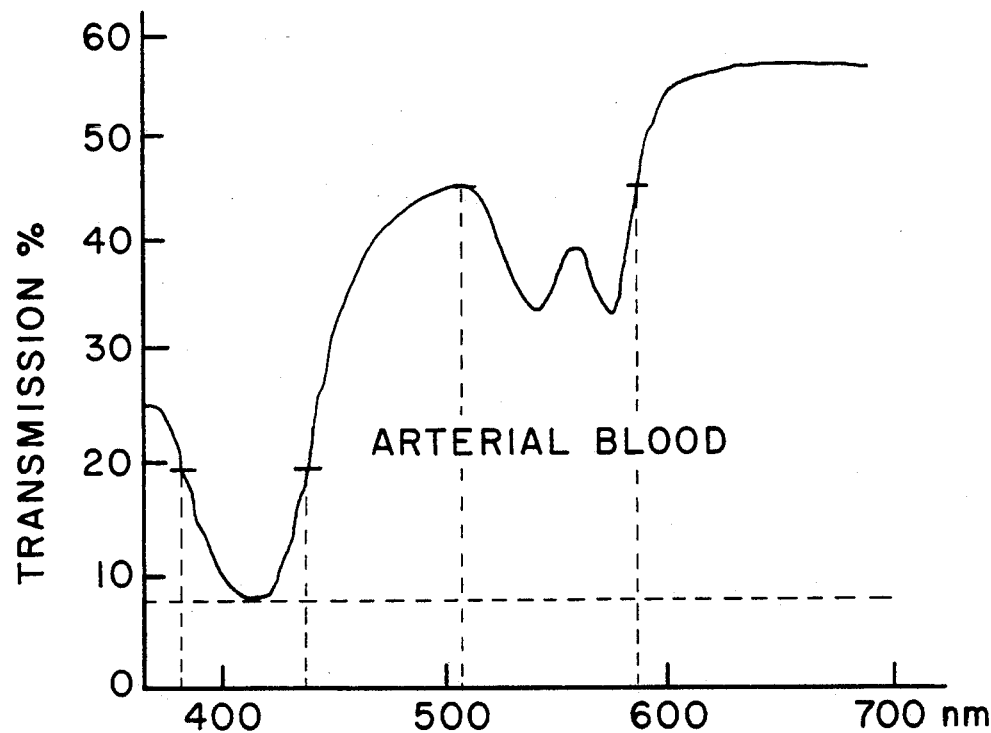
FIG. 8a depicts the absorption spectra of arterial blood.
Figure 8B:
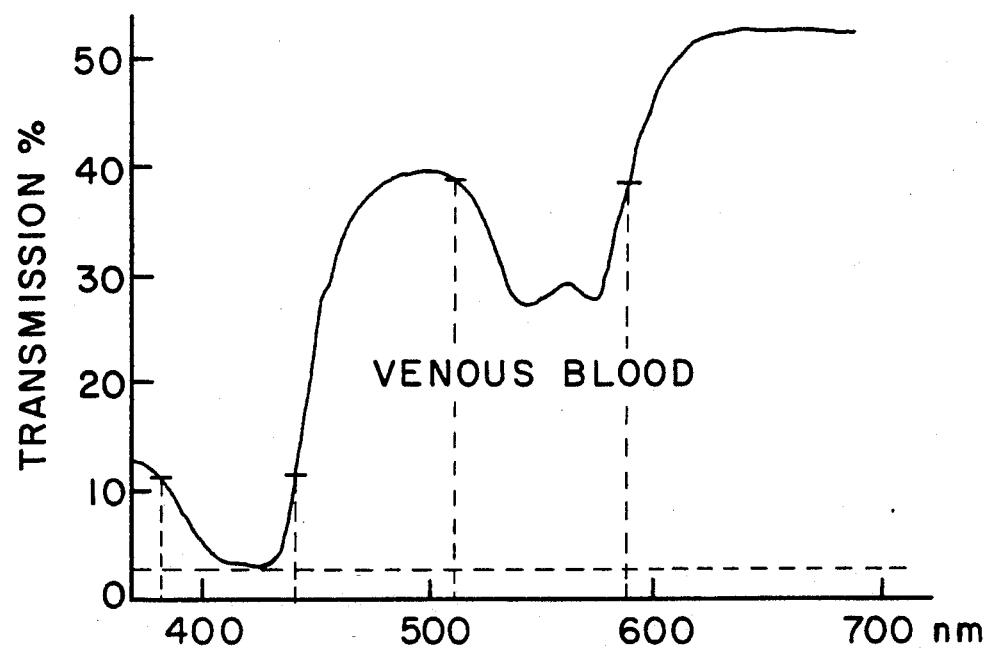
FIG. 8b depicts the absorption spectra of venous blood.

FIG. 8 shows the transmission spectrum through a 0.2 mm thick layer of arterial (top) and venous (bottom) blood, both diluted in saline solution to 20% concentration. To make fluorescence spectrography through such an absorber, always present in in vivo studies (except if temporarily displaced by another liquid), creates great difficulties. According to an aspect of the invention, therefore, there is selected at least one pair of different wavelengths having the same absorption factor, which is used for the detection on the sample. Two such pairs are indicated in the drawings.

EXAMPLE II

Five classes of pathologically verified samples of plaque, where O denoted a normal artery wall, and I–IV denoted progressed disease in increasing measure, were measured for fluorescence in different wavelengths. The intensities were divided pairwise as shown in FIG. 9. As apparent from the Figure, the correlation degree varied very much dependent on the wavelength choice. F1–F4 are influenced by blood reabsorption, F5 and F6 are not. F5 and F6 show that there are true spectral differences between these tissue types and not just variations in the amount of blood. Also the relative uncertainties (denoted at one standard deviation) are smaller for the blood compensated pairs F5 and F6.

EXAMPLE III

Figure 10:
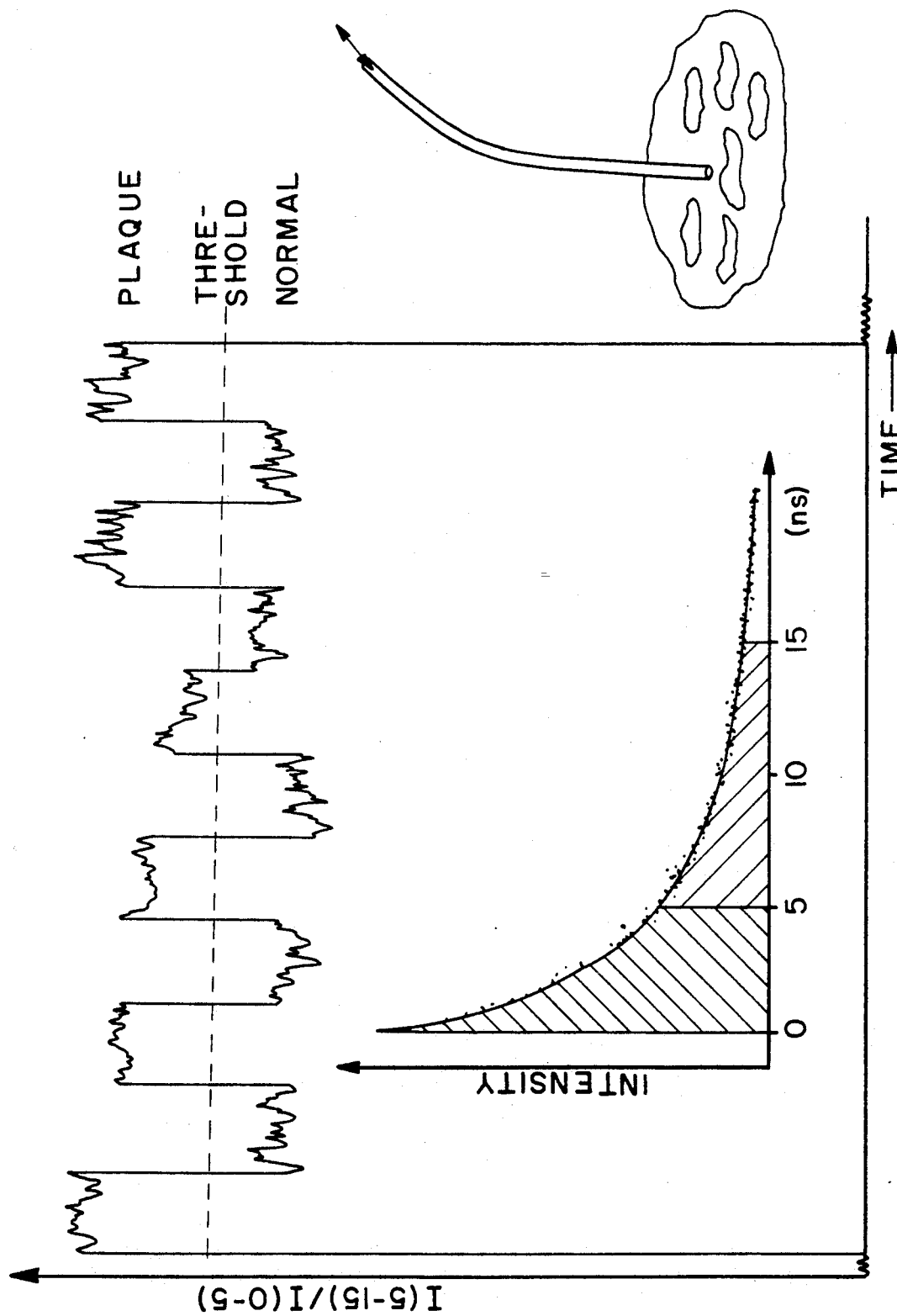
FIG. 10 shows the separation possibilities in time spectra for a selected wavelength.

It could be shown that the fluorescence is long-lived enough to allow the use of a short-pulse nitrogen laser (PRA Model LN 250, $\Delta t_p = 3$ ns) in conjunction with a dual channel boxcar integrator (Stanford Instruments Model SR 250) to distinguish between "early" and "late" fluorescence at 400 nm. Excitation was made at 337 nm. A Hamamatsu Model R 105 photomultiplier was used. One detection channel was timed at 0-5 ns, while the second one was covering 5-15 ns as indicated in FIG. 10, where a decay curve obtained with the picosecond system is inserted. In the boxcar system, the ratio between "late" and "early" fluorescence (which has all the virtues of a dimensionless quantity) is formed and displayed on a strip-chart recorder. In FIG. 10 the signal is shown as the fiber-optic probe schematically shown is moved from point to point over an artery sample identifying the plaque regions. As can be seen, a theshold value can be established above which the plaque criterion is fulfilled and steering signals to a plaque ablation laser can be provided.

Figure 11:
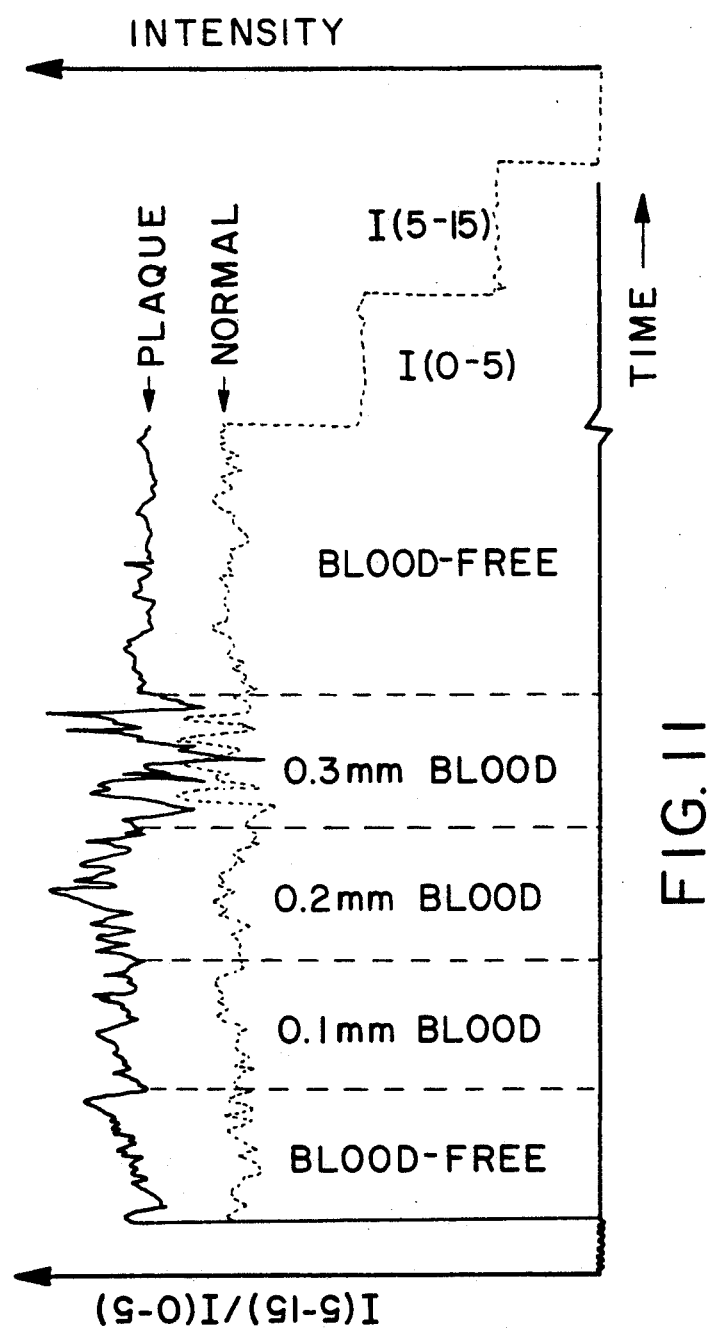
FIG. 11 shows the elimination of blood disturbance when using a temporal analysis (ratio between late and early flourescence) for a selected wavelength.

The data in FIG. 10 were obtained for a specimen rinsed from blood to allow a clear visual inspection of the atherosclerotic and normal wall regions. A second investigation was performed on two selected typical spots where recordings through a blood field were taken. The results are shown in FIG. 11. Again, recordings of the late-to-early fluorescence ratio were made. As can be seen, the ratios stay constant and separated from each other up to a blood layer thickness of 0.3 mm (60 μm of undiluted blood). For thicker layers the individual signals become so small that no useful signal-to-noise ratio can be obtained. In the right part of the Figure, the individual boxcar channel signals are also shown for blood-free normal vessel wall. From FIG. 8 it is clear, that these signals at 400 nm become very weak when the layer of undiluted blood is thicker than several tens of micrometers. Thus the optical diagnostic must rely on the fiber being kept close to the sample, or the observation field must be flushed with saline in a blocked peripheral artery. In both cases the diagnostic system must clearly indicate when the signal is too low. On the other hand, a system built on the principle given above yields a reliable guidance independent of blood once the fibre tip has been brought in sufficient vicinity of the artery wall and the system is switching itself into a data-recording mode.

The above Examples demonstrate that reliable diagnostic of arteries is possible even in the presence of blood, by means of using a plurality of spectral fluorescence intervals, (1) by a zero difference absorption wavelength pair and/or (2) two temporal spectrum intervals.

The teachings of the invention have now been shown in single-channel embodiments as to space, one can say, in one-pixel embodiments. However, the same principles can also be used in multi-pixel embodiments, i.e. for spatial resolution.

EXAMPLE IV

Figure 12:
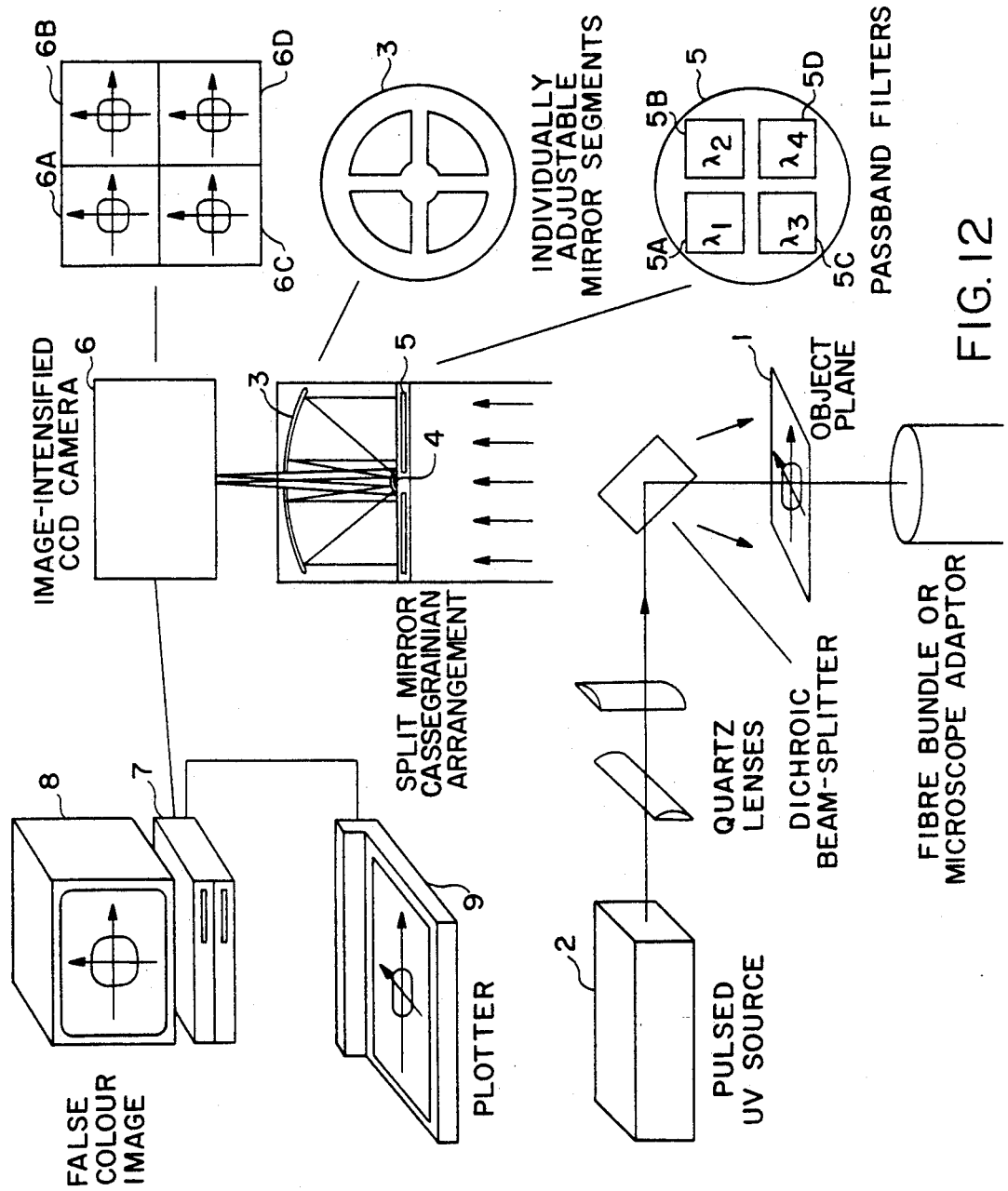
FIG. 12 shows an imaging embodiment of the invention.

FIG. 12 shows a schematic view of apparatus as known in principle from EP-A-0 199 767. A sample in an object plane 1 is irradiated from a pulsed UV source 2. The sample is imaged by a mirror 3, which is split and differentially angled in order to make four separate images 6A-6D after reflexion on a Cassegrain mirror 4 on to an image intensifier CCD camera 6, coupled to a computer 7. The radiation to each of the segments of mirror 3 are led through four filters 5A-5D. The images 6A-6D therefore represent images in four different wavelength bands. The detector is a modern microchannel plate image intensifier. The intensifier is gateable down to at least 5 ns.

Figure 13:
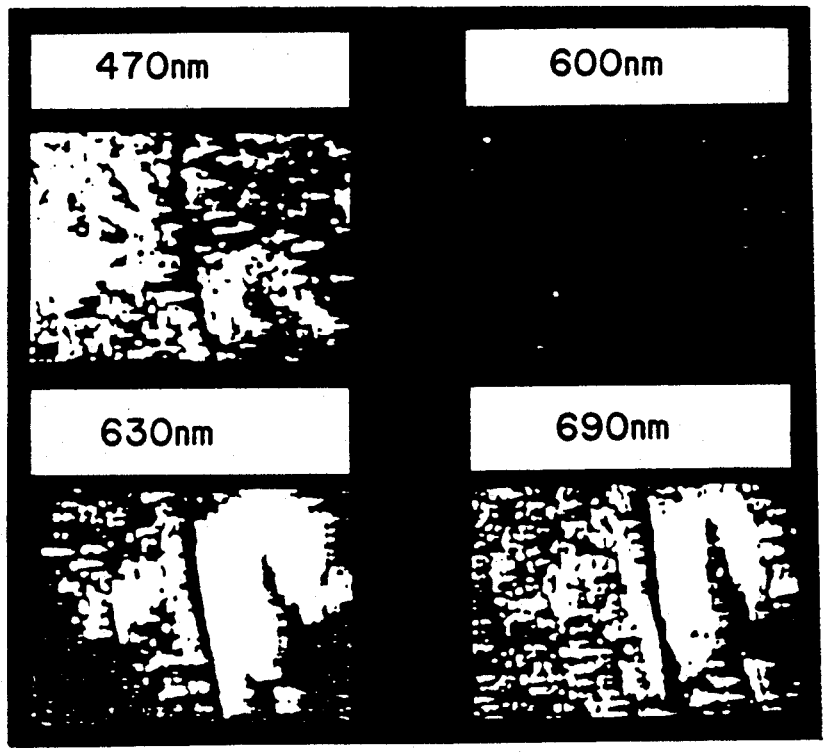
FIGS. 13–15 demonstrate imaging detection of cancer.
Figure 14:
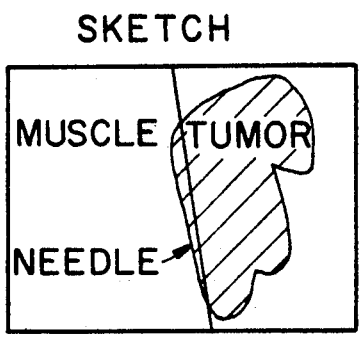
Figure 15:
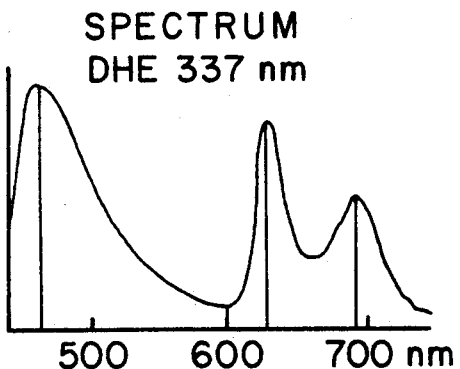

In FIG. 13-15 is shown an exemplary result for a rat malignant tumour. FIG. 13 shows four "monochrome" images, in wavelengths 470, 600, 630 and 690 nm. The significance of those wavelengths is apparent from the spectrum in FIG. 15, regarding the fluorescence from that type of tumour. The four colours were combined into a false-colour image on a monitor (not shown). A sketch of the image as visually seen is shown in FIG. 14. The actual size of the imaged region was about 10 mm.

In this Example, a Delli-Delti image intensified CCD camera system and an IBM compatible computer with a Data Translation Model DT 7020 vector processor were used.

Figure 16A:
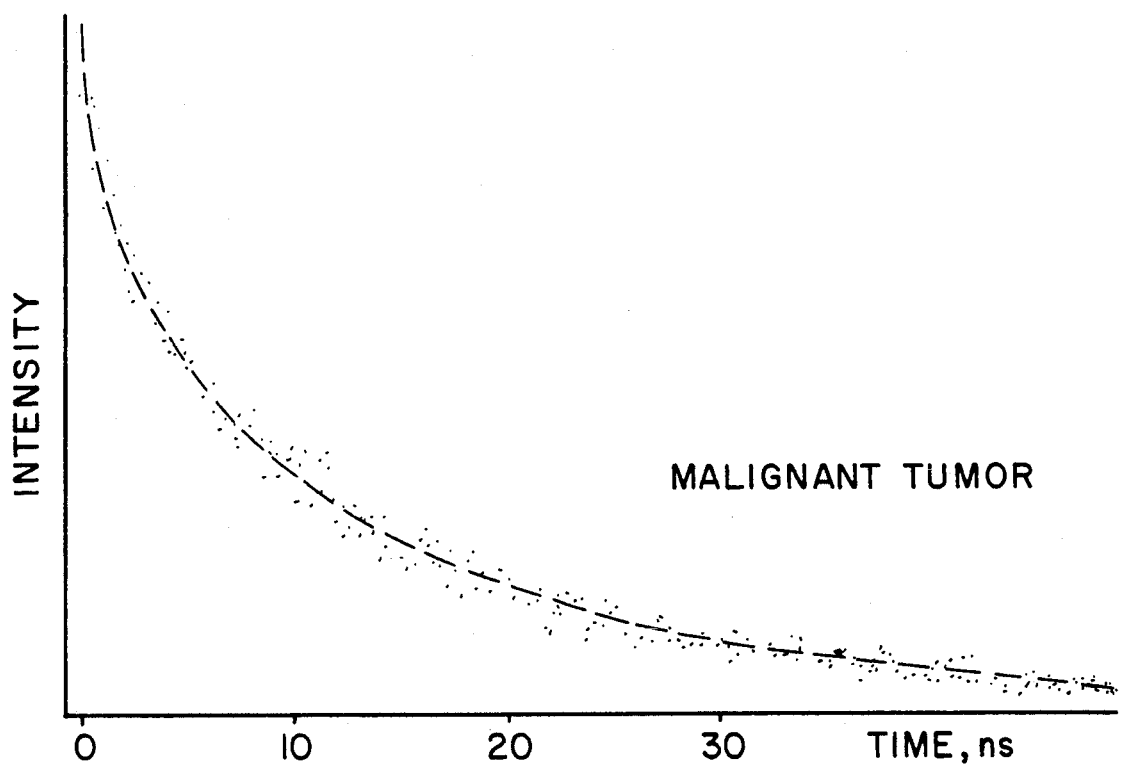
FIGS. 16a and 16b show the different temporal spectrum behaviour in normal and malignant tumour tissue.
Figure 16B:
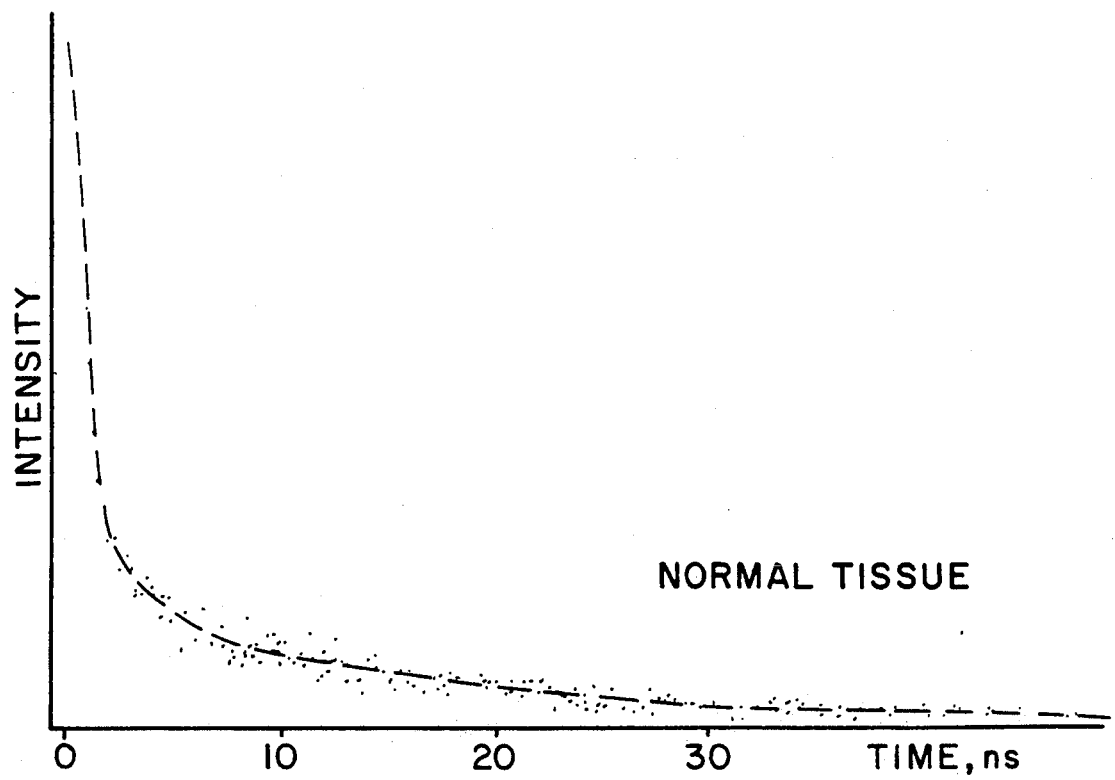

It has been observed experimentally that the 630 nm fluorescence band in tumourous tissue (due to porphyrins) is much more long-lived than background fluorescence at the same wavelength, as shown in FIG. 16. The temporal differences for plaque and normal vessel were already discussed in connection with FIGS. 5 and 10. Clearly it is possible, further to increase the detection efficiency also in imaging equipment, by using the gating facility of the camera tube as already remarked and divide "late" fluorescence images by "early" fluorescence images.

We claim:

1. A method for determining tissue character by fluorescence, comprising the steps of
   i. exciting the tissue with a laser wavelength below 500 nm,
   ii. detecting a fluorescence intensity within a plurality of predetermined spectral intervals for obtaining a plurality of numerical intensity values, at least two of said predetermined spectral intervals comprising spectral intervals centered on wavelengths having substantially equal absorption values in blood,
   iii. performing an arithmetic operation on said numerical intensity values including at least one division operation.

2. The method of claim 1, wherein said predetermined spectral intervals comprise wavelength intervals.

3. The method of claim 1, wherein said predetermined spectral intervals include intervals in time, starting and ending in predetermined relationship to the end of a duration of a pulse from said laser.

4. The method of claim 1, wherein said predetermined spectral intervals comprise a plurality of wavelength intervals, each wavelength interval being detected in a predetermined interval in time, starting and ending in predetermined relationship to the end of a duration of a pulse from said laser.

5. The method of claim 1, wherein the tissue is excited with a laser wavelength below 400 nm.

6. The method of claim 1, wherein said detection step comprises simultaneous detection of fluorescence intensity for said plurality of spectral intervals from a multitude of surface elements in a sample illuminated by the said laser pulse.

7. A device for determining tissue character by fluorescence, comprising
   i. a laser illumination source,
   ii. detector means for detecting fluorescent light from a sample illuminated by said source in a plurality of predetermined spectral fluorescence intervals for obtaining a plurality of intensity values, at least two of said predetermined spectral intervals being centered in wavelength on a pair of wavelength values having substantially equal absorption values in blood, iii. arithmetic and/or logical means for performing an operation on said plurality of intensity values, including at least one division operation, for obtaining a numerical value characteristic of the tissue character of the sample.

8. A device according to claim 7, comprising spectral resolution means for predetermining detector wavelength intervals for said plurality of spectral intervals.

9. A device according to claim 7, wherein said laser illumination source is a pulsed source, and comprise time resolution means for predetermining time spectral intervals of fluorescence starting and ending in predetermined relationship to pulses from said source.

10. A device according to claim 7, wherein said detector means are multi-channel means for simultaneous detection of fluorescence intensity for said plurality of spectral intervals from a multitude of surface elements in a sample illuminated by the said laser illumination source.

* * * * *